United States Patent [19]
Rizzo, III

[11] Patent Number: 5,597,381
[45] Date of Patent: Jan. 28, 1997

[54] METHODS FOR EPI-RETINAL IMPLANTATION

[75] Inventor: Joseph Rizzo, III, Boston, Mass.

[73] Assignee: Massachusetts Eye and Ear Infirmary, Boston, Mass.

[21] Appl. No.: 72,321

[22] Filed: Jun. 3, 1993

[51] Int. Cl.$^6$ .................................................. A61F 2/14
[52] U.S. Cl. ............................. 623/4; 128/745; 128/898; 607/53; 607/116; 607/118
[58] Field of Search .................................. 623/4; 607/2, 53, 607/115, 116, 118; 128/745, 898

[56] References Cited

U.S. PATENT DOCUMENTS

| | | | |
|---|---|---|---|
| 4,628,933 | 12/1986 | Michelson | 623/4 X |
| 5,016,633 | 5/1991 | Chow | 623/4 X |
| 5,024,223 | 6/1991 | Chow | 623/4 X |
| 5,109,844 | 5/1992 | de Juan, Jr., et al. | 623/4 X |

OTHER PUBLICATIONS

B. Glaser, et al., "Transforming Growth Factor β-2 for the Treatment of Full-thickness Macular Holes", Jan. 1992, *Ophthalmology*, vol. 99, pp. 1162–1173.

J. Vander, et al., "A Method for Induction of Posterior Vitreous Detachment During Vitrectomy", 1992, *Retina*, vol. 12, pp. 172–173.

H. Lincoff, et al., "Morphological Effects of Gas Compression on the Cortical Vitreous", Aug. 1986, *Arch Ophthalmol.*, vol. 104, pp. 1212–1215.

*Primary Examiner*—Mary Beth O. Jones
*Attorney, Agent, or Firm*—Choate, Hall & Stewart

[57] ABSTRACT

A method for epi-retinal implantation of an object into a subject is disclosed. The method includes rendering the normally transparent cortical vitreous visible and separating at least a portion of a cortical vitreous of the subject away from an adherent retinal surface to form an epi-retinal space between the retina and the separated cortical vitreous material. An object to be implanted may be introduced into the epi-retinal space and the object engaged with a surface of the retina. In preferred embodiments, the object may then be adhered to the surface of the retina. A method for implantation of a neural contact structure for contact with neural tissue, for example, neural tissue of the retina within which are ganglion cells to be electrically stimulated is also described. The contact structure comprises a first portion for attachment to a first bodily location, such as the inner surface of the retina, and a second portion interconnected with the first portion via an interconnection and being held in contact with the neural tissue. The interconnection exhibits a weak restoring force which in conjunction with the geometry of said second portion provides a preselected desired pressure of contact against the neural tissue. As adapted for the retina, the interconnection exhibits a weak restoring force developed in response to curvature of the interconnection along the inner radius of the retina.

17 Claims, 9 Drawing Sheets

METHODS FOR EPI-RETINAL IMPLANTATION

BACKGROUND OF THE INVENTION

This invention relates to surgical procedures for implanting devices that interface with neural tissue.

Surgery within the eye usually is designed to remove damaged or altered tissue. The most common examples include removal of the lens that becomes cloudy with age (i.e., cataract), or removal of the jelly (i.e. vitreous) that fills the back portion of the eye behind the lens. Nevertheless, surgery within the eye has the potential to be of use in procedures to artificially stimulate and activate neural tissue in the eye by implanting prosthetic devices which pass pulses of electrical current through electrodes. For instance, some forms of blindness involve selective loss of the light sensitive transducers of the retina. Other retinal neurons remain viable, however, and potentially may be activated by placement of a prosthetic electrode device on the inner (i.e., toward the vitreous) retinal surface. This placement must be mechanically stable, minimize the distance between the electrodes and the neurons, and avoid undue compression of the neurons.

Vitreous is a jelly-like substance that can largely be extracted with special instruments using conventional procedures. There is, however, a transparent, thin (100 micron) layer of vitreous that is closely applied to the inner retinal surface. This layer cannot be so easily removed. This so-called "cortical" vitreous is a trellis-like scaffolding covering the entire inner surface of the retina. The cortical vitreous is highly sensitive to irritation as caused by pressure, other mechanical stimulation, or inflammation. The cortical vitreous, if subjected to even slight pressure, will contract and pull away from the retina, with potentially disastrous results.

Because the cortical vitreous is transparent, methods of identifying it have relied upon using an intraocular suction cannula with a flexible tip. The cannula can be connected to an aspiration system and the tip of the cannula can be positioned several millimeters above the inner surface of the retina. Suction is applied and if a layer of cortical vitreous is present, the cannula bends because the dense, but transparent, cortical vitreous blocks the proximal region of the cannula. This particular method is described in more detail in Glaser, et al., *Ophthalmology*, 99 (7) 162–1173 (1992). Nevertheless, this method utilizes significantly higher levels of suction (greater than twice the standard amount) to identify, and/or engage a small area of the cortical vitreous under the cannula. This high level of suction, when applied almost directly to the retinal surface, is potentially dangerous. Pulling on the cortical vitreous with this extreme pressure, or inducing traction by application of heat, can lead to retinal damage, including formation of holes and retinal detachment.

Moreover, the above method facilitates cortical vitreous removal from a small area only. Removal from a wide field requires more aggressive manipulation and suction contact. Unfortunately, the tightly adherent and thin layer of cortical vitreous cannot be removed by currently available vitrectomy units because the suction ports that remove vitreous are recessed 1 mm or more from the end of the instrument. Removal of the cortical vitreous has been attempted using enzymatic digestion of the cortical vitreous but this method is uncontrolled, giving highly variable results. Use of expansile intraocular gas to dissect the cortical vitreous has also been suggested, but further studies have also shown highly variable results (Lincoff, H., *Fortschr. Ophthalmol.*, 81: 95–98, 1984).

Nevertheless, in spite of the difficulties with methods of removing the cortical vitreous, it is just this cortical vitreous which must be removed in order for prosthetic, or other devices to be successfully implanted directly onto the retinal surface. In particular, if a retinal electronic implant is to function without inducing contraction of the cortical vitreous and retinal detachment, the implant needs to be in intimate contact with cells on the surface of a denuded retina, i.e. one from which a cortical vitreous has been removed.

Furthermore, removal of the cortical vitreous may also have a therapeutic effect, particularly in diabetic patients with diabetic retinopathy. Jalkh, A. et al., *Arch. Ophthalmol.* 100: 432–434, 1982. In this condition, abnormal blood vessels and/or cells grow across the scaffolding of the cortical vitreous, leading to contraction of the cortical vitreous and retinal detachment. Absence of the cortical vitreous, as occurs as a natural phenomenon in older patients, is known to prevent most of the severe complications of the diabetes. Surgery, therefore, designed to remove the cortical vitreous, would seem desirable. Yet despite the availability of methods to remove the cortical vitreous, its removal has not been advocated since the techniques are considered too dangerous for regular application, as evidenced by the lack of support in medical journals for their use.

Unfortunately, even if the cortical vitreous can be removed without noxious effects, by the methods summarized above, excessive manipulation of the underlying retina is also problematic since the retina is an extraordinarily fragile part of the brain, with a consistency of wet tissue paper. In particular, retinal neurons are extremely sensitive to pressure; they will die if even a modest intraocular pressure is maintained for a prolonged period of time. Glaucoma, which is one of the leading causes of blindness in the world, can result from a chronic increase of intraocular pressure of only 10 mm Hg.

The eye also generates significant centrifugal force with saccadic (i.e., jerky, high velocity) eye movements, up to several hundred arc degrees/second, and an implant would tend to slide over the retinal surface if not securely attached. Furthermore, the retina if it is perforated or pulled will itself tend to separate from the underlying retinal pigment epithelium and be rendered functionless. Thus, any method of attaching an object to the retina (i.e., using, for example, tacks) may not be practical, primarily because of the typically high downward pressure that such a device would exert on the retina, which inevitably compromise the retinal neurons.

A reliable method of removing the cortical vitreous has, to our knowledge, never been conclusively demonstrated by histological examination. Moreover, a method of implanting an object securely, but without excessive pressure, onto an inner retinal surface (i.e., epi-retinal) that is free of cortical vitreous has, to our knowledge, not heretofore been demonstrated by in vivo examination.

SUMMARY OF THE INVENTION

It is an object of the invention to provide a method which allows a surgeon to remove cortical vitreous of an eye and expose the retina in a visually guided and controlled, manual dissection.

It is a further object of the invention to provide a method of rendering the transparent cortical vitreous visible so that it can be manually dissected away from the inner surface of the retina.

It is another object of the invention to provide a method of implanting an object directly onto an inner surface of a retina that is free of cortical vitreous.

To accomplish these objectives, the present invention is a method of removing the cortical vitreous. In another aspect, the invention is a method of removing the cortical vitreous and implanting an object onto the inner retinal surface in a controlled way. In general, the present method relies on a natural property of the cortical vitreous, i.e., the contractile nature of the normally transparent cortical vitreous, to render the cortical vitreous visible, to enhance its own removal, and to provide access to the retina for implantation and subsequent adhesion of an object.

In one aspect, the invention provides a method for removing the cortical vitreous. The method includes transforming the cortical vitreous from its normally transparent condition to a visible condition by inducing the natural, contractile properties of the cortical vitreous using mechanical stimulation. Mechanical stimulation induces formation of visible collagen fibrils within the normally transparent cortical vitreous. Next, at least a portion of a cortical vitreous is separated away from an adherent retinal surface to form an epi-retinal space between the retina and the separated cortical vitreous. In a further step, an object to be implanted is introduced into the epi-retinal space and the object is then engaged with a surface of the retina that lacks the cortical vitreous. In preferred embodiments, the object is then adhered to the surface of the retina.

In another aspect, the invention pertains to a method of epi-retinal implantation of an object, comprising inducing contraction of at least a portion of the normally transparent cortical vitreous so that the portion is rendered visible. The visible cortical vitreous is then separated away from the underlying retinal tissue, and then removed using standard vitrectomy instruments. An epi-retinal space is then enlarged manually by blunt dissection and an object is introduced into the epi-retinal space. After this, the object is engaged with the retinal tissue that is free of the cortical vitreous and preferably adhered to the retinal tissue free of the cortical vitreous. In the preferred embodiments of the invention, the step of inducing contraction comprises introducing an inducing element onto a surface of the cortical vitreous. The inducing element is an object that contacts a portion of the cortical vitreous under conditions sufficient to induce contraction of fibrils within the cortical vitreous. The contraction of the cortical vitreous allows the cortical vitreous to be more easily manipulated and removed from the retinal surface.

A preferred means for adhering the object to the retina includes providing an object that is hydrophilic, such as for example, a hydrogel or other polymer. This material will adhere to the retina after intraocular fluids are removed in standard fashion partly by virtue of its hydrophilic properties. In another embodiment, adhesion is enhanced by gluing the object to the retinal tissue or photocoagulating a portion of the retina to the object.

A further aspect includes a method for implanting a low-pressure neural contact structure onto neural tissue of a retina of an eye. The method includes removing vitreous material of the eye to expose the retina and associated cortical vitreous; inducing contraction of at least a portion of the cortical vitreous of the eye so at least a portion of the cortical vitreous separates from the retina; forming an epi-retinal space defined between the retina and said separated cortical vitreous; enlarging the epi-retinal space; introducing a low-pressure neural contact structure into the epi-retinal space; and engaging the low-pressure neural contact structure with retinal tissue that is free of the cortical vitreous. The preferred low pressure neural contact structure includes a first portion for attachment to a first location on a surface of the retina, and a second portion interconnected with the first portion via an interconnection and being held in contact with a second location on the retina adjacent to cells to be stimulated, the interconnection exhibiting a weak restoring force developed in response to curvature of the interconnection along an inner radius of the retina, whereby the weak restoring force in conjunction with a geometry of the second portion provides a preselected desired pressure of contact against the retina.

Another aspect of the invention is the combination of at least a portion of a retina of an eye that is free of cortical vitreous and an object implanted directly into that portion of the retina free of the cortical vitreous. The implanted object may include a hydrogel. In one embodiment, the implanted object comprises a first portion for attachment to a first location on a surface of the retina, and a second portion interconnected with the first portion via an interconnection and being held in contact with a second location on the retina adjacent to cells to be stimulated. The interconnection exhibits a weak restoring force developed in response to curvature of the interconnection along an inner radius of the retina, whereby the weak restoring force in conjunction with a geometry of said second portion provides a preselected desired pressure of contact against said retina. The first and second portions together comprise an integral structure which may be a cantilever or other structure.

In other embodiments, the hydrogel or other polymer defines a layer which encapsulates at least a portion of the object.

BRIEF DESCRIPTION OF THE DRAWINGS

FIG. 1 is a schematic cross-sectional illustration of a mammalian eye and the method of the invention for removing the cortical vitreous and implanting an object.

DETAILED DESCRIPTION OF THE INVENTION

The present method utilizes the natural, contractile properties of the cortical vitreous as an aid to enhance its removal from the retinal surface. The contractile properties of the cortical vitreous are well known, primarily due to the presence of contractile proteins such as collagen which make up an important part of the cortical vitreous matrix, and contraction of which is normally destructive. The present method also relies upon the contractile properties, induced in a controlled manner, of the normally transparent cortical vitreous to render the cortical vitreous visible and to assist in the formation of an epi-retinal space. The term "epi-retinal" ("epi"-on, on the outside, above) refers to that space formed by a disengaged cortical vitreous on one side and the intact retinal tissue on another side.

FIGS. 1A–1D represent in schematic illustration a general method of the present invention which includes separating at least a part of the cortical vitreous of the eye away from adherent inner retinal tissue to form an epi-retinal space. An object is introduced into the epi-retinal space and the object is then engaged with the surface of the retina that is free of the cortical vitreous.

Figure 1A:
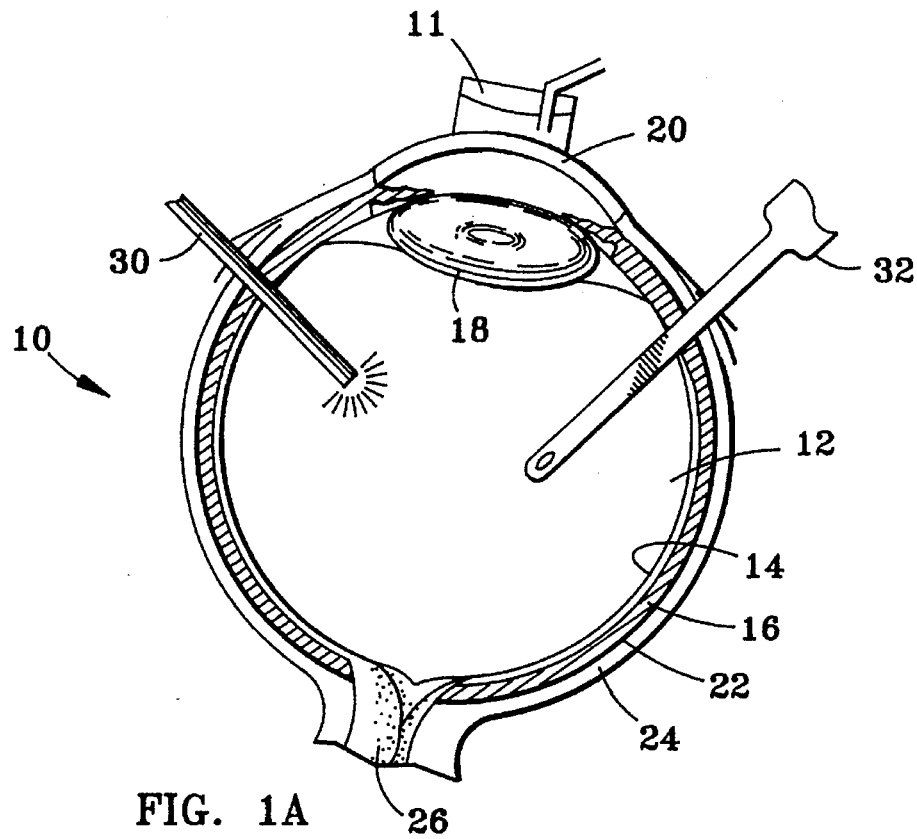
FIG. 1A is a cross-sectional view showing a first step of the method for removing the cortical vitreous.

FIG. 1A is a schematic cross-section of a mammalian eye 10 with the vitreous 12 enclosed within the eye, the cortical vitreous 14 being that part of the vitreous on the inner surface of the retina. The retina 16 is immediately adjacent to the cortical vitreous 14, the cortical vitreous being about 100 microns thick, transparent, and covering the entire inner retinal surface. Other structures such as the lens 18, cornea 20, choroid 22, sclera 24 and optic nerve 26 are also represented. A surface contact lens 11 is shown to permit focusing on the back of the eye.

The first step in the method is to remove the core vitreous (i.e., the vitreous exclusive of the cortical vitreous) from within the eye (FIG. 1A). Removal of the core vitreous is a well known and well characterized procedure. Vitrectomies are described by Machemer, R. et al., *Trans. Am. Acad, Ophthalmol. Otolaryngol.* 75: 813, 1971, the entire contents of which are incorporated herein by reference. Briefly, a standard closed vitrectomy is performed using at least three ports placed at the pars plana. One port is used for infusion of air and/or fluids (e.g. balanced salt solution) via cannula to maintain internal pressure within the eye. The other ports are used to pass instruments into the eye such as a fiber optic light tube 30.

The cortical vitreous is then rendered visible by inducing contraction of at least a part of the cortical vitreous. Contraction is induced by mechanical stimulation (i.e., contacting the cortical vitreous with an inducing element). This inducing element is a solid object that, when placed in contact with the cortical vitreous, will irritate the cortical vitreous and induce the collagen component of the cortical vitreous to form visible fibrils. Fibril formation, often induced within 5–10 minutes, spreads to more peripheral areas of the retina, a process that can be observed to emanate from the area where the inducing element contacts the cortical vitreous.

Figure 1B:
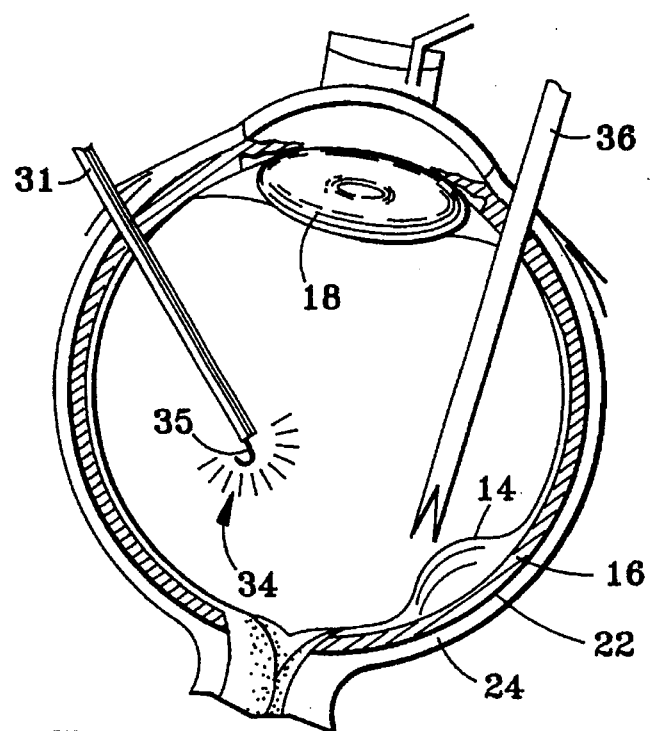
FIG. 1B is a cross-sectional view showing a second step of the method in which the cortical vitreous is rendered visible.

Referring now to FIG. 1B, a fiber-optic spatula 31 (Escalon Trek Medical, Mukwonago, Wis.) that provides intraocular illumination 34 is introduced. Spatula 31 has a distal end 35 that permits blunt dissection. An intraocular forceps 36 is introduced into the eye to contact the cortical vitreous 14. The transparent cortical vitreous is made visible by mechanical stimulation, as by stroking the cortical vitreous 14 with the intraocular forceps 36. After several minutes, thin fibrils (not shown here) within the cortical vitreous become visible and they are seized and lifted slightly with the intraocular forceps 36.

Next, the end 35 of the spatula 31 is placed under the elevated fibrils of the cortical vitreous 14. The fibrils are pulled backward while the spatula is advanced under the plane of the cortical vitreous. In essence, the fibrils are used to peel the cortical vitreous off the retinal surface. The same sets of maneuvers are used repeatedly to strip the cortical vitreous from a wide area, as much as is desired or possible, given the limitations of the view into the eye.

The collagen fibrils represent physico-chemical changes in the state of the cortical vitreous (i.e., contraction and/or aggregation). Because the cortical vitreous is tightly adherent to the retina, some of the fibrils are cut to prevent the contracting and/or aggregating cortical vitreous from pulling too strongly against the retina.

Elevation of the fibrils of the cortical vitreous creates a posterior vitreous detachment (usually at least 1 mm from the retinal surface), defining an epi-retinal space. The degree and rate of separation of the cortical vitreous can be controlled. The epi-retinal space is large enough (several mm) to comfortably accommodate standard vitrectomy instruments. That is, after the contractile response is initiated and the cortical vitreous is peeled back, the clear separation of the cortical vitreous from the surface of the retina ( the epi-retinal space) is wide enough so that a standard vitrectomy is used to extract the sheet of cortical vitreous that has been formed during the procedure.

Contraction of the cortical vitreous results in a thick and easily visible edge or surface. Moreover, the cortical vitreous spontaneously elevates from the surface of the retina as it contracts. Thus, little pressure is needed to elevate the cortical vitreous as compared to other methods which require a slight vacuum or aspiration to obtain contact with the elevated cortical vitreous.

Figure 1C:
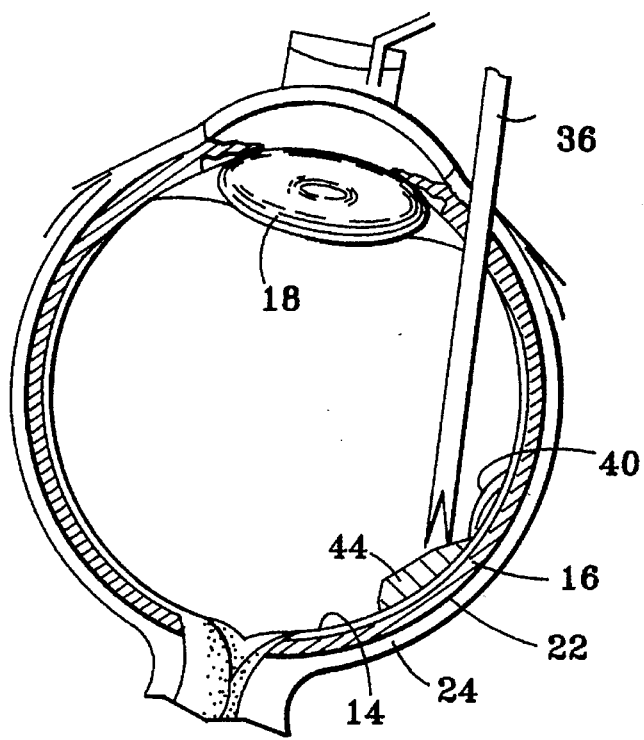
FIG. 1C is a cross-sectional view of an alternate step in which the cortical vitreous is rendered visible.
Figure 1D:
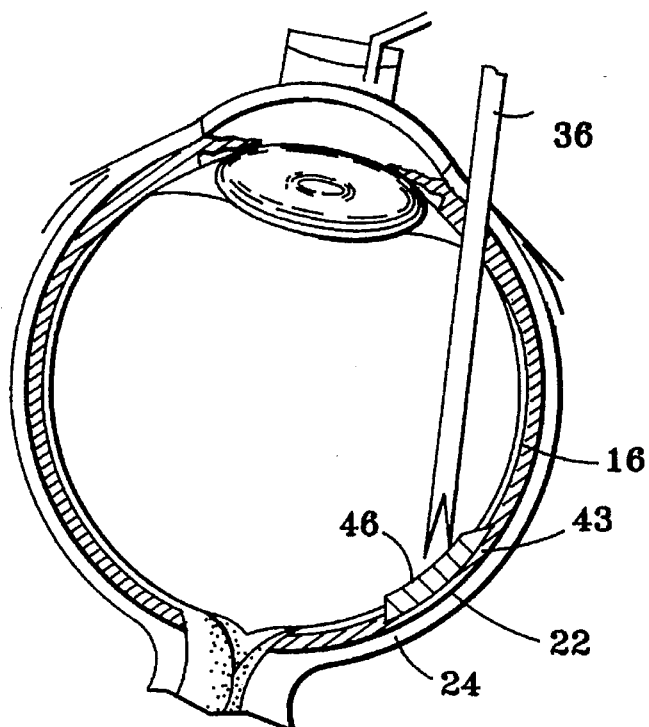
FIG. 1D is a cross-sectional view showing a fourth step of the method in which an object is engaged with the cortical vitreous.

Referring to FIG. 1C, alternately, or in addition, the contraction of collagen fibrils over a wider area (as great as 10 mm or more) may be induced by placing a small, inert object 44, or "inducing element" on the surface of the cortical vitreous. This object may be made, for example, of a polymer such as polyimide approximately 100 microns thick and about 2 mm by 4 mm in area. By placing the inducing element 44 with a forceps 36 onto the cortical vitreous 14, a more complete contractile response of fibrils 40 is induced around the border of the inducing element within minutes. The element 44 is later removed.

Figure 8:
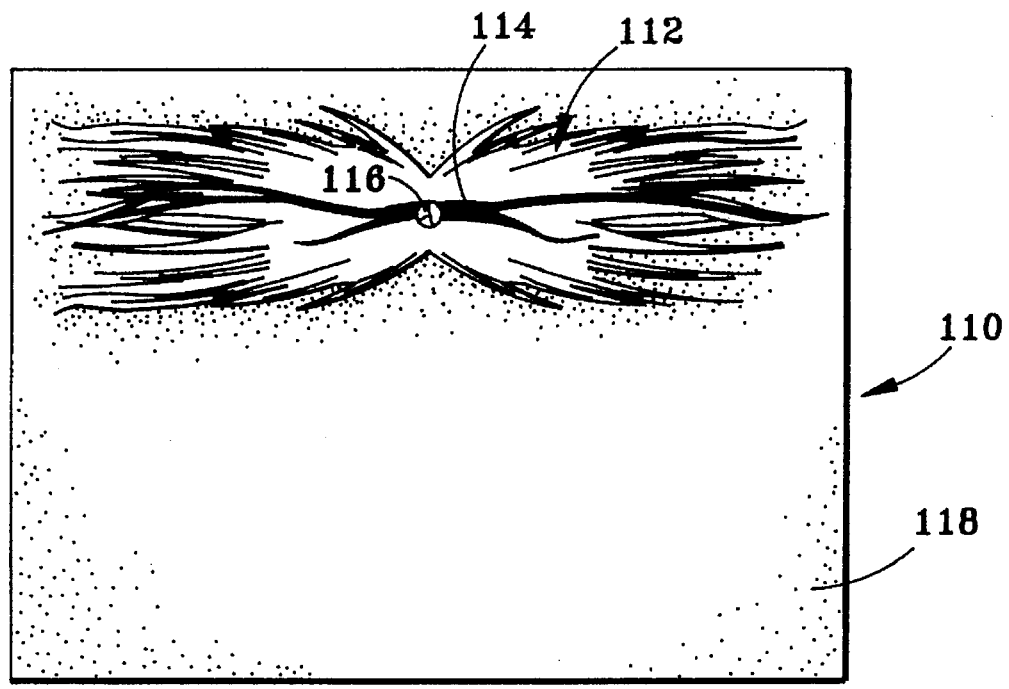
FIG. 8 is an artist's rendition of the field of an intraocular microscope showing a first step of the method.
Figure 9:
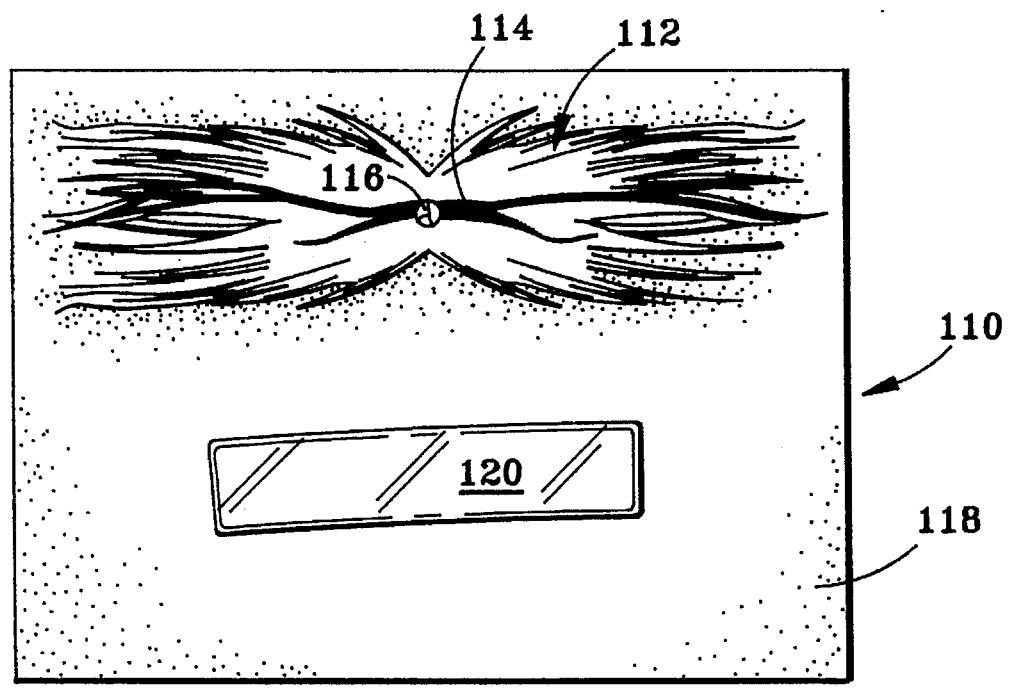
FIG. 9 is an artist's rendition of the field of an intraocular microscope showing a second step of the method.
Figure 10:
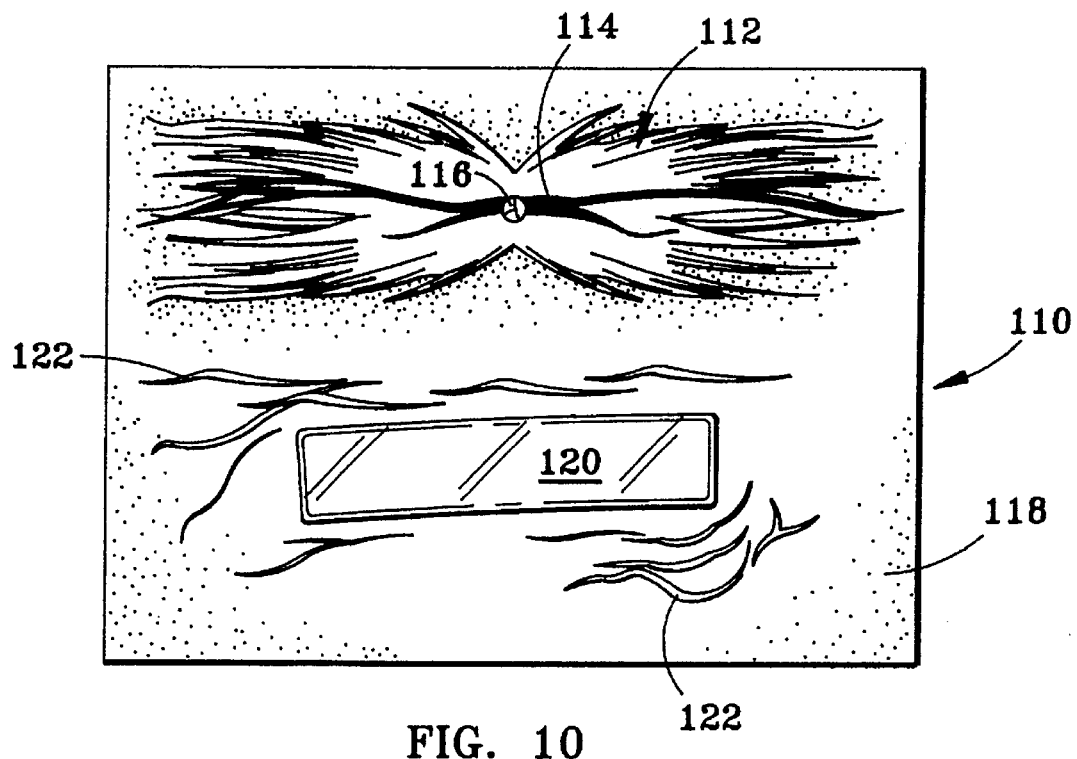
FIG. 10 is an artist's rendition of the field of an intraocular microscope showing a third step of the method.

During an operation on a rabbit eye to remove the cortical vitreous, an artist observed the intraocular field through the lens of the intraocular microscope and drew the images observed therein. The artist's drawing of FIG. 8 is a rendition of the rabbit retina 110, removal of the core vitreous having already been performed, leaving a thin layer of transparent cortical vitreous 118 over the entire retina. FIG. 9 is a drawing of a rabbit retina 110 which shows additional anatomic detail such as the specialized area called the myelinated nerve fiber bundle 112, the white lines at the top through which blood vessels 114 traverse. The optic nerve 116 is the small circular structure at the center of the myelinated bundle. Removal of the core vitreous has already been performed, leaving a thin layer of transparent cortical vitreous 118 over the entire retina. This Figure also shows a rectangular piece of polyimide 120 (the inducing element) placed inferior to the optic nerve 116 on the cortical vitreous that overlies the retina. Within several minutes, the previously transparent cortical vitreous develops thin fibrils 122, as shown in the artist's drawing of FIG. 10. These fibrils represent contracted collagen fibers.

The intraocular forceps is then used to elevate the inducing element, thus creating an epi-retinal space under the element to pass the spatula, which is positioned to develop a plane under the cortical vitreous. This plane may be widened by the same peeling movements described above. Removal of the inducing element requires that the fibrils be cut with, for example, an intraocular scissors (e.g., Escalon Trek Medical, Mukwonago, Wis. 53149). Thus, induction of contraction provides a visually guided, controlled, manual dissection of the cortical vitreous.

Figure 11:
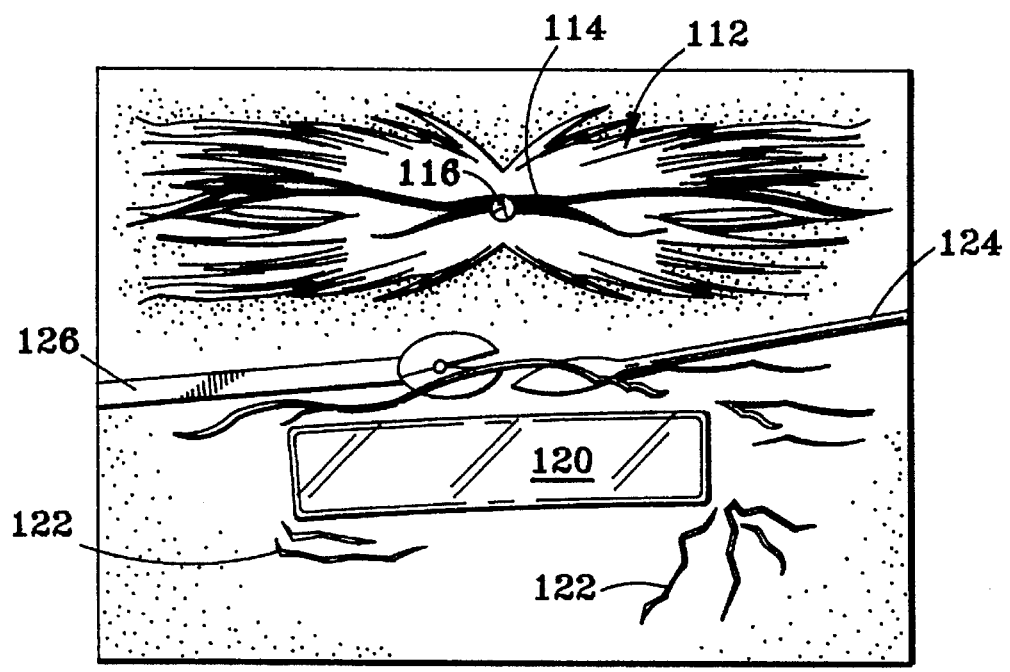
FIG. 11 is an artist's rendition of the field of an intraocular microscope showing a fourth step of the method.
Figure 12:
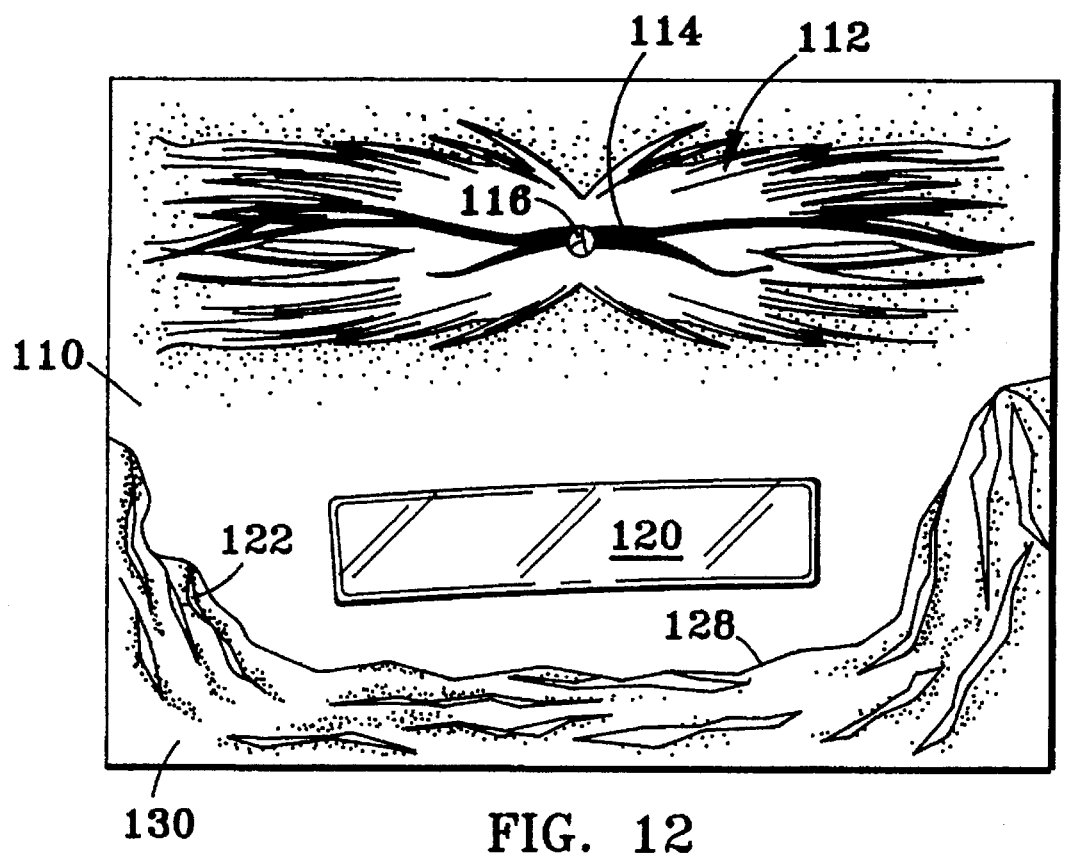
FIG. 12 is an artist's rendition of the field of an intraocular microscope showing a fifth step of the method.

The artist's drawing of FIG. 11 shows how the fibrils 122 are seized with an intraocular forceps 124 and cut with an intraocular scissors 126. The fibrils need to be cut to prevent the contracting cortical vitreous from pulling too strongly against the retina, which can lead to a retinal hole and retinal detachment. At this stage, the fibrils are seized and the spatula is used to peel off the cortical vitreous, as described above. In the rabbit, at least 10 mm in diameter can be denuded of the cortical vitreous. The artist's drawing of FIG. 12 shows the polyimide 120 resting over the retina 110 denuded of cortical vitreous. The edge 128 of the remaining, contracted cortical vitreous 130 is clearly visible in the field as the curved line of demarcation. The polyimide can be seized with an intraocular forceps and removed from the eye.

The object to be implanted is large compared to the openings in the eye provided for the core vitrectomy. Thus, the object is introduced into the eye via an incision at the junction of the cornea and the sclera. The object is advanced into the anterior chamber (i.e., the space in front of the iris) and then lowered under visual guidance onto the surface of the vitreous-free retina. In particular, the step of engaging the object (FIG. 1D) onto the denuded retina involves use of, for example the intraocular forceps 36 to introduce an object 46 onto the retina 16 and engage the object 46 with that portion of the retina 16 that is free of the cortical vitreous. The term "engage" refers to an orientation of the object which is, at least in part, on the inner surface 43 of the retina, which surface faces the (now excised) cortical vitreous material. The term also refers to objects which are partially or wholly embedded or implanted into the retinal tissue lacking a cortical vitreous.

An epi-retinal implant can then be positioned on the denuded bed of the retina. A variety of objects may be engaged with the retina according to the methods of the invention and are not intended to limit the scope of the invention in any way. For example, prosthetic devices which might contain silicon, silicon nitride and the like may be employed, any of which may contain electrodes made of electrically conducting materials such as conductive polymers or conductive metals such as, for example, gold, platinum and iridium. Further, a variety of sustained release implants made of biocompatible polymers may also be used.

Once engaged with the surface of the retina, the preferred method includes the steps of adhering the object to the portion of the retina that is free of the cortical vitreous. The term "adhere" refers to a technique that ensures maintenance of the engaged object at the site of engagement and prevents migration or other movement of the object from the initial site of engagement. There are several methods suitable for adhering the object to the retinal surface.

The most preferred method relies upon selecting an object having chemical and/or physical properties that enable it to adhere to the retinal surface without use of glue or tacks. The most preferred materials that serve this purpose are polymers such as polyvinylalcohol (PVA) or hydrogels; hydrophilic polymers or other materials that are commonly used in a variety of other biomedical applications.

By themselves, hydrogel objects can be particularly useful because the hydrogel can be manufactured to provide for delivery of low molecular weight materials from the hydrogel into the retinal tissue. Such low molecular weight materials can include drugs, proteins, or other therapeutic compounds. In particular, connective tissue growth factors such as, for example, epidermal growth factor, transforming growth factor (alpha), fibroblast growth factor, platelet-derived endothelial cell growth factor, insulin-like growth factor, nerve growth factor and the like, may be used to induce or augment adhesion of the implanted object to the retinal surface that is free of the cortical vitreous.

The hydrogel which forms the preferred object can be prepared from a wide variety of materials. For example, three dimensional hydrophilic polymeric products ranging from a lightly or sparingly cross-linked network to a relatively highly cross-linked system are useful in the practice of the methods of the invention. Such products are carefully prepared by controlled polymerization techniques which utilize a feed comprising at least one of the following illustrative monomers: monomers of an acrylic acid or methacrylic acid with an alcohol having an esterifiable hydroxyl group and at least one additional hydroxyl group such as the mono-polyalkylene glycol monoesters of methacrylic acid and acrylic acid, e.g. ethylene glycol monomethacrylate, substituted acrylamides and methacrylamides and others known in the art. See, for example, U.S. Pat. No. 4,298,002 (Ronel, et al.). The polymerization reaction may be conducted in the presence of a cross-linking agent as illustrated by, for example, ethylene glycol, diacrylate, divinylbenzene, and the like.

Hydrogel polymers are advantageous because they can be lathed to a fine dimensions of thickness and curvature, they are highly flexible, transparent, non-toxic in the eye (see, for instance, Example 2) and have a long history of safe use as soft contact lenses. Moreover, hydrogel has considerable promise as material that can be anchored to the surface of the retina and to which one could bond electrodes and/or silicon retinal implants to aid patients suffering from certain forms of blindness, as discussed more fully below. In particular, after fluid-gas exchange the interior spaces of the eye are dry but the surface of the retina contains a small amount of water due to the surface tension of the water. It is the hydrophilic properties of the hydrogel that allow it to absorb the layer water on the retinal surface, thus effectively bonding the hydrogel object to the surface thereof. Other materials may also be used such as silicone, or other polymers.

Fluid within the eye is naturally replenished post-operatively. The degree of adhesion of the hydrogel may be lost under these circumstances because both sides of the hydrogel will now absorb water. We have determined that adhesion may be increased, however, by local heating of the border (i.e., the peripheral edge of apposition between the hydrogel and retinal surface) of the implanted object with a near infrared laser. A preferred operating condition uses a 300 mW laser directing 300 msec pulses of approximately 50 microns in diameter. The pulse may be delivered by any commercially available ophthalmic laser using an intraocular fiber optic probe. This type of photocoagulation probably causes changes in the proteins at the junction of the retina and the object that help increase the adherence of the object to the retina. Additionally, adhesion using the laser may be increased by placing perforations in the implanted object, allowing cells of the local environment to extend processes through the material to form a local scar.

Several types of glues can be used to create adherence on the surface of the retina. Cyanoacrylate glues have been used in intraocular surgery for years but are known to be locally damaging to biological tissue. These glues however must be administered under free control with the use of small syringes and a cannulas, although some glues require a mixture of two components which can be performed with a double barrelled syringe.

Another feature of the present invention is a method for mixing a multi-component glue within the eye itself using hollow vesicles that contain the individual components.

Preparation of coacervate vesicles, liposomes, or hollow microspheres are well known to those of ordinary skill in the art. For example, organic polymeric porous microcapsules for encapsulating various materials are represented by U.S. Pat. Nos. 4,251,387, and 4,743,545. If the microspheres are porous, it is generally sufficient to merely suspend the microspheres in a liquid carrier medium containing the individual glue components and to allow the glue components to diffuse by capillary action from pores in the walls of the microspheres into the space within the microsphere. If liposomes are used, for example, the lipsomes can be generated in a suspension or dispersion of the particular glue component material.

The vesicles containing the glue components are introduced at the site of implantation using the same techniques and cannulated apparatus as described previously. When the vesicles containing the glue components are in place, laser light is applied to the vesicles. The intensity and wavelength of the particular laser light is selected so that the vesicles are broken or dispersed and the two components mixed together in situ. This laser technique has the advantage of forming the glue in a spatially constrained manner.

After engagement and adherence of the object to the retinal surface, the eye is resutured and the internal volume of the eye is filed with air, gas, balanced salt solution or synthetic (i.e., non-contractile) vitreous using conventional techniques. The internal gas may be air or one or more biologically inert gases. In particular, as done routinely in human retinal detachment surgery, a syringe containing, for example, a fluorocarbon gas such as perfluoroethane ($C_2F_6$) or octafluoropropane ($C_3F_8$) may be connected to an infusion cannula and up to about 2.5 ml can be injected through the infusion cannula into the eye. Gas and air are allowed to escape from the eye by way of, for example, a 30-gauge needle introduced through the pars plana in the 10:00 o'clock meridian. Alternately, a plurality of injections of a smaller volume can be administered. The fluorocarbon gas expands intraocularly which provides a strong force to keep the eye fully inflated and the retina and attached object in place. This gas is slowly replaced by natural fluids over a period of weeks.

Preferably, the method also includes a way of following the health of the eye after implantation. The electroretinogram (ERG: both full field and focal method) is the standard technique for testing the responsiveness of the retina. Further techniques for testing the health of the eye include, for example, fluorescein angiography, best-corrected Snellen visual acuity, visual evoked potentials (VEP's), clarity of cornea, and intraocular pressure.

A preferred object that can be implanted using the present method is a low pressure neural contact structure, the details of which are described in co-pending application Ser. No. 08/234,725, entitled "Low Pressure Neural Contact Structure", fried Apr. 28, 1994, the entire contents of which are incorporated herein by reference. The structure and function of this particular low pressure neural contact is described briefly below.

Figure 2A:
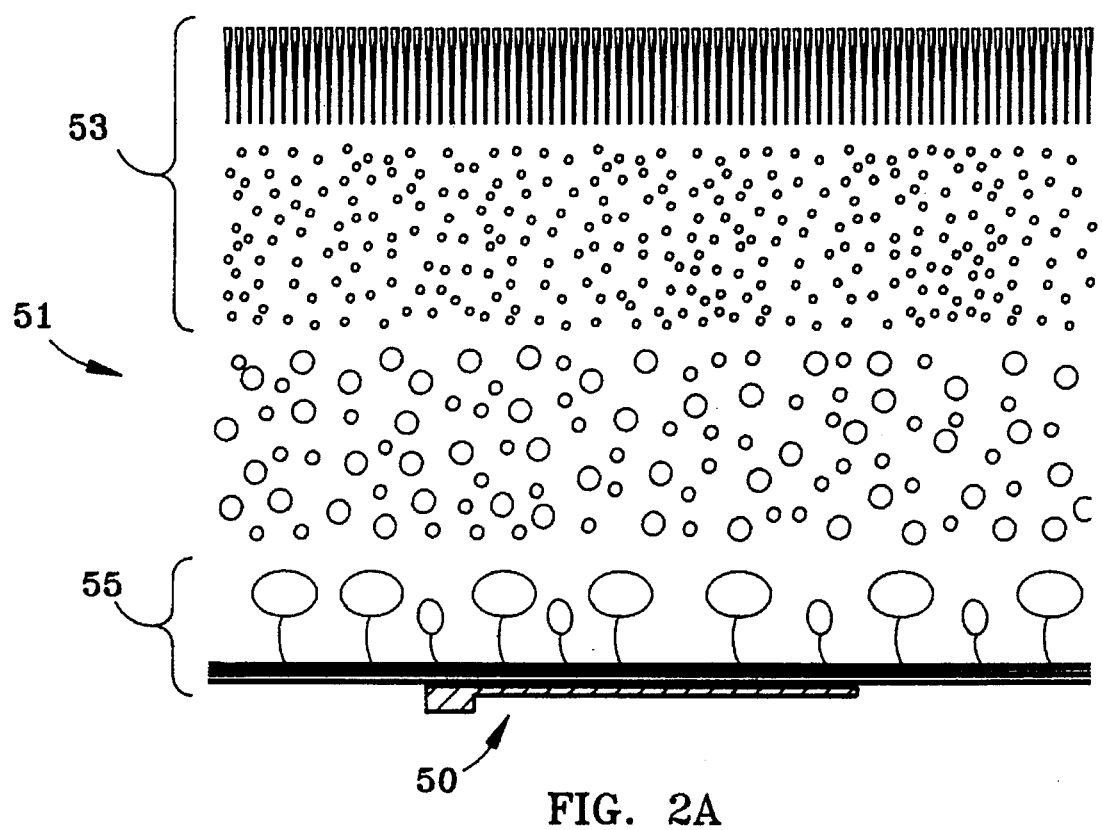
FIG. 2A is a cross-sectional view of the neural contact of the invention in place on the retina.
Figure 2B:
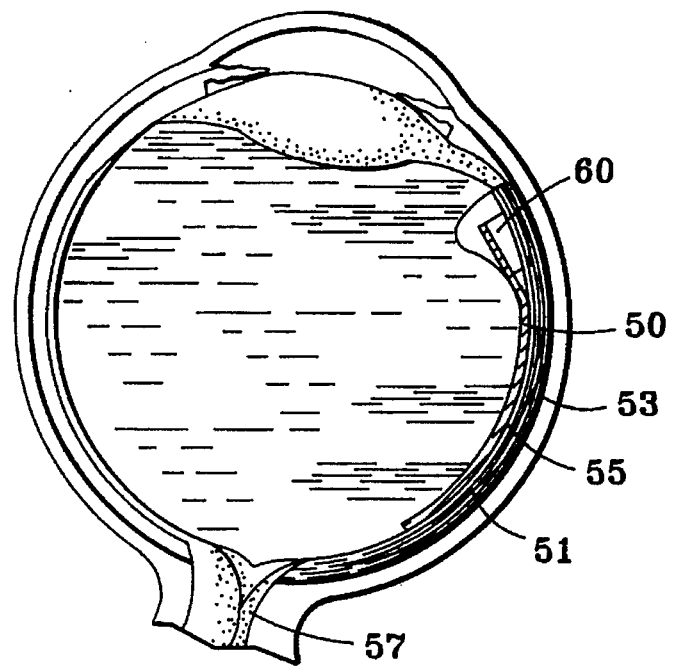
FIG. 2B is another cross-sectional view of the neural contact of the invention in place on the retina.

Referring to FIGS. 2A and 2B, there is shown the low-pressure neural contact of the invention 50 adapted for stimulation of retinal neural cells. As shown in the figure, the retina 51 consists of several layers of cells. The outermost layers 53 (away from the geometric center of the eye) contain the rods and cones, which are the cells that sense the presence of light and initiate a nerve signal that passes to the brain. The innermost layers 55 (adjacent to the cortical vitreous) primarily contain the ganglion cells, which have axons extending into the brain via the optic nerve 57. Between the inner and outer retinal layers are many different cell types that process neural signals from the rods and cones before the signals are sent to the brain. Light coming from the front of the eye must traverse the retina in order to reach the rods and cones. The corresponding signals generated by the rods and cones then travel to the inner retina on the way to the brain.

There are at least two types of retinal diseases which are of a nature which lends them to treatment via a retinal prosthetic implant positioned on the inner retinal surface using the methods of the invention. The first, macular degeneration, is the leading cause of blindness in the Western World. Age-related macular degeneration affects approximately one in ten people over the age of 60 years. Visual loss due to this disease is progressive, and frequently causes loss in the "legal blindness" range. The pathology of macular degeneration affects the rods and cones, as well as a pigmented layer of cells upon which the rods and cones are aligned. However, the ganglion cells and their connections to the brain remain intact, and being located just below the inner surface of the retina, are opportunely located to be affected by electrical currents that are applied to the surface of the retina. A method using the invention may take advantage of this arrangement by placing an implant on a retinal surface that is free of cortical vitreous, the implant contacting the retinal surface for stimulation of those ganglion cells. In effect, this scheme bypasses the damaged area of the retina.

The other disease that is treatable with an implant using the inventive contact is retinitis pigmentosa. The cause of this inherited disease is not known, but the damage caused by the disease is also at the level of the rods and cones. Retinitis pigmentosa results in a progressive loss of vision over decades, leaving many sufferers almost totally blind. A medical treatment is not available for either retinitis pigmentosa or macular degeneration.

Figure 3A:
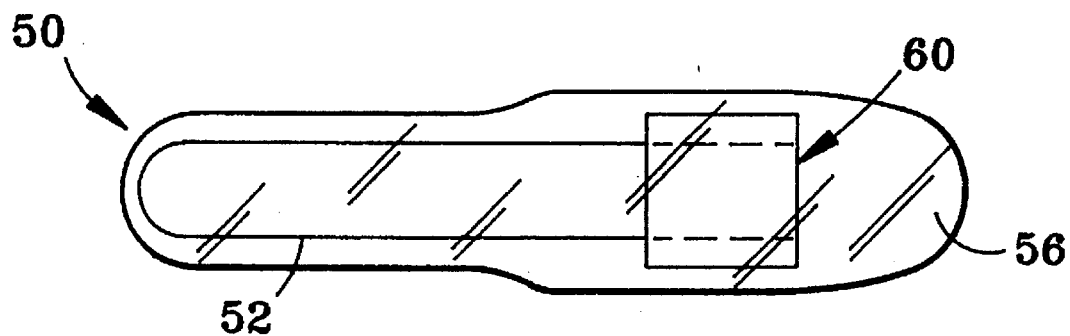
FIG. 3A is a planar view of one embodiment of the neural contact of the invention.
Figure 3B:
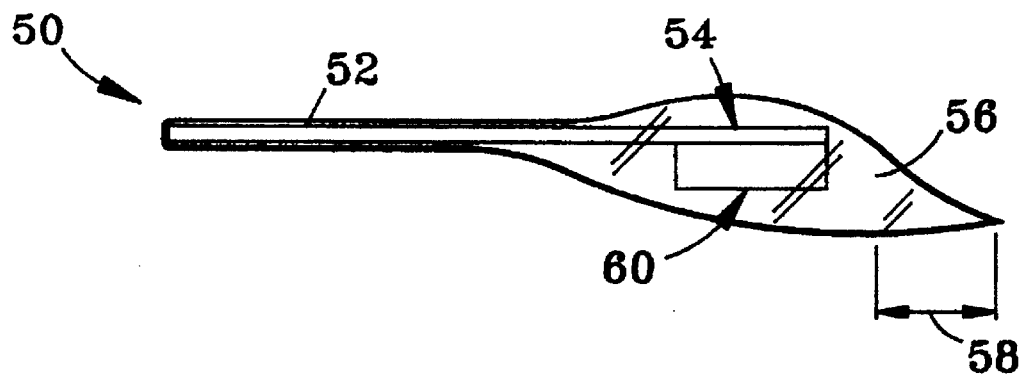
FIG. 3B is a side view of one embodiment of the neural contact of the invention.

Also referring to FIGS. 3A and 3B, the neural contact 50 consists of a thin cantilever 52 which gently conforms to the curvature of the retina while at the same time maintaining low pressure contact with the surface of the retina that is free of cortical vitreous. One portion 60 of the cantilever 52 is physically engaged with the retina (not shown), while the remaining area of the cantilever is held in contact with the retina by a restoring force which develops along the cantilever's length-wise axis in response its curvature when the cantilever is engaged on the retina.

In order to use this cantilever design effectively, a stable, cortical vitreous-free area of the retina is required. With this scheme, the area of physical attachment to the retina is distanced from the rest of the cantilever, which supports, e.g., stimulating electrodes 54, whereby any damage caused to the neurons by the attachment will have no effect on the somewhat remote neurons under the rest of the cantilever— these neurons may be interfaced and stimulated. The attachment portion 60 is thus suited for supporting various circuitry, e.g., data and input power processors, which are not directly involved in neuron stimulation, while the remaining area, being separated from this portion, ideally supports the stimulating electrodes for stimulating the retinal ganglion cells.

The cantilever structure may range from a few millimeters to 5 centimeters in length, and preferably between 0.5–2 centimeters in length. The width of the cantilever may be between 0.5 mm–1 cm, and should be about 2 mm; this width being determined by the two-dimensional curvature of the eye, because the cantilever spring element will only bend in one direction. The cantilever width does not need to be uniform along the cantilever length, however. For example, the cantilever may have a more narrow central region separating the attachment portion from the stimulating region. In addition, appropriate width contours along the length of the cantilever could be designed to produce a standard force magnitude along the length of the cantilever.

The restoring force exerted by the cantilever on the retinal surface free of cortical vitreous is ideally prespecified using an appropriate cantilever geometry, thickness, and material. Examples of materials suitable for the cantilever include silicon, silicon nitride, silicon carbide, sapphire, diamond, or other materials which exhibit some flexibility and which may be processed to render them biocompatible. In addition, the materials should be compatible with microfabrication techniques. The specific choice of materials will dictate the thickness of the cantilever for providing uniform, low pressure on the retinal surface. If, for example, silicon is used as the cantilever material and silicone is used to encapsulate the cantilever (see below), the silicon and silicone portions could both be between 2–40 µm-thick, with the silicon layer being ideally between 5–15 µm-thick and the silicone layer being ideally between 5–25 µm-thick.

Given these geometric guidelines, the cantilever geometry is particularly specified to provide both an adequate retinal contact and a minimum amount of pressure on the retina. This pressure should ideally be below 10 mm Hg; the ganglion cells are adversely impacted by prolonged pressures above this level. For example, glaucoma is a significant cause of blindness which would result from elevation of intraocular pressure for an extended time.

In particular, the force of the cantilever against the retina should be slightly greater than only the weight of the cantilever assembly. In addition, the weight of the assembly is minimized to thereby minimize both static and dynamic forces, i.e., accelerations, due to movement of the eye. Use of low-density materials such as silicone achieve this minimized acceleration and also minimize gravity effects on the contact pressure. The force of the tip of the cantilever opposite the attachment portion may be determined as follows:

$p = \delta E b h^3 / 4 L^2$ where p=force
E=Young's modulus
b=cantilever width
h=cantilever thickness
L=cantilever length
δ=deflection of tip from unbent position By selection of the cantilever geometry and area, a, the pressure, p/a, may be precisely and predictably specified for a particular material. The shape of the cantilever may be varied to precisely tailor the force along the length of the cantilever. This can be done using common numerical design modeling and simulation software packages to match the design goals of the cantilever with the shape of the eye and the preferred materials for the cantilever. Because pressure is a function of applied force per unit area, widening the structure in a particular area would tend to decrease the pressure in that local area.

As discussed above, the cantilever supports electrodes for stimulating ganglion cells in a location distant from the site of cantilever attachment to the retina. Such electrodes may be of any suitable design which would provide electrical current stimuli to the ganglion cell bodies. An array of electrodes 54 may be positioned on one end 60 of the cantilever 50. Each electrode is connected via, for example, conducting traces, to circuitry located at the attachment end 60 of the cantilever 52. As discussed above, the circuitry may include pulse generation and power circuitry. The circuitry and electrodes may be discrete electronic pieces which are assembled on the cantilever, or they may be fabricated as an integrated body with the cantilever. Using a discrete assembly process, flip chip bonding using one of a variety of well-known techniques is preferred because such a method would minimize the overall mass of the cantilever structure.

Encapsulation of the cantilever, electrodes, and electronics is essential for biocompatibility of the structure with the retinal environment. Referring again to FIGS. 3A and 3B, hydrogels and silicones are a good choice for an encapsulation material 56 based on their performance during direct immersion in saline environments. Hydrogels and silicones can be mixed to provide a wide range of mechanical properties, and can be micromachined in much the same manner as conventional electronic materials to a prespecified desired geometry. Fluorocarbons and polyesterimides may also be good encapsulation materials; their use with standard electronic materials, such as silicon dioxide, requires a silane coupling agent that could create stable bonds between these materials and silicon dioxide in an aqueous environment. Other biocompatible materials may also be selected as an encapsulation material.

The hydrogel 56, or other material, should be very flexible and soft, and should extend beyond the edges of the cantilever structure 52 by an amount equal to at least its thickness, and more preferably 4–5 times its thickness. The overhanging area 58 may be perforated to allow residual vitreous to ooze through and hold it stable once it is in place on the retina. This is particularly advantageous as it is crucial to maintain a precise positioning of the contact structure. The overhang edge also has the advantage of being better matched to the mechanical impedance with the neural tissue, and thereby minimizes the trauma or damage which the structural edges may cause to the retinal surface. Referring specifically to FIG. 3B, the hydrogel or silicone layer is thickest at the point of attachment to the retina, and tapers away from the attachment area.

Other embodiments for the low pressure neural contact structure may be readily appreciated by persons having ordinary skill in the art and are within the scope of the invention. Suitable structure geometries should ideally be capable of carrying various stimuli or recording electronics and electrodes. Furthermore, the site of attachment of the structure to the retina should be distanced from the site of active neural interface. Power and signal processing circuitry, which may mechanically compromise the neural tissue, should be relegated to the remote attachment site. And optimally, the contact structure should ensure that any stimulating electrodes are pressed against the retina with a known degree of pressure that remains constant despite variations in surgical procedure, despite variations in the strength of the contact attachment to the retina, and despite flexing, deformation, growth and aging of the eyeball.

The invention will now be illustrated by the following, non-limiting examples.

EXAMPLE 1

Material and Methods

The experimental work described herein was done in the rabbit which has a highly reactive vitreous. This property was used to advantage to reveal in an accelerated manner the contractile response of the vitreous that so often leads to failure in human retinal surgery. In the rabbit, the initial contraction of the cortical vitreous occurs in one small area and within minutes the contraction spreads over a wide area.

Dutch-belt rabbits are obtained from one of several regional breeding farms. Rabbits are usually in the 2.5 kg weight range. The animal is anesthetized with intramuscular injections of xylazine and ketamine, used in standard doses. An intravenous cannula is placed in an ear vein to provide fluid during the surgery. The eye is prepped in a sterile fashion and the animal draped so that only the eye to be operated upon is exposed.

EXAMPLE 2

Use of Electroretinograms

This example illustrates the effect of implantation on the responsiveness of the retina. The amplitude of the ERG is dependent on the density of photoreceptors (rods and cones) in the area of stimulation. ERG's were measured using conventional procedures. In rabbits, the density of photoreceptors is considerably less than in humans and stimulation of a small spot of the retina (i.e. focal ERG) produced amplitudes that were just above basefine noise when 42 Hz stimulation was used, which is the standard for human testing. We then measured the amplitude while varying the frequency from 2–52 Hz. The signal-noise ratio was improved 8-fold by lowering the stimulating frequency to 17 Hz, and this improved ratio has permitted us to more accurately follow the health of the retinas.

The method is a full-field electroretinogram waveform using a 6 degree light flickering at 17 Hz over the region of the visual streak. ERG's were obtained pre- and -post-implantation of a hydrogel implant. The implant was positioned within the visual streak and post-operative recordings were made from the area of the implant.

Two animals who underwent successful implantation with hydrogel material were followed by measuring the ERG. One rabbit has been monitored over 4.5 months and the full-field ERG (the response derived from the activity of the entire retina) decreased from 100 uV pre-implant to 10 uV post-implant. Focal stimulation of the retina also reduced 10 fold over the same time period. The explanation for the decline in strength of the ERG is unknown; it is suggestive of a diffuse reduction in activity of the retina, as might occur from a toxic response. One other rabbit underwent the same procedure with hydrogel implant and was followed for nearly a month with very little change in ERG amplitudes. In this latter case, normal focal response of the retina was recorded.

EXAMPLE 3

Photomicrography and Electron Microscopy

A series of electron micrographs were taken during the procedures described above. A transmission electron microscope was used at a magnification of 16,500 x.

Figure 4:
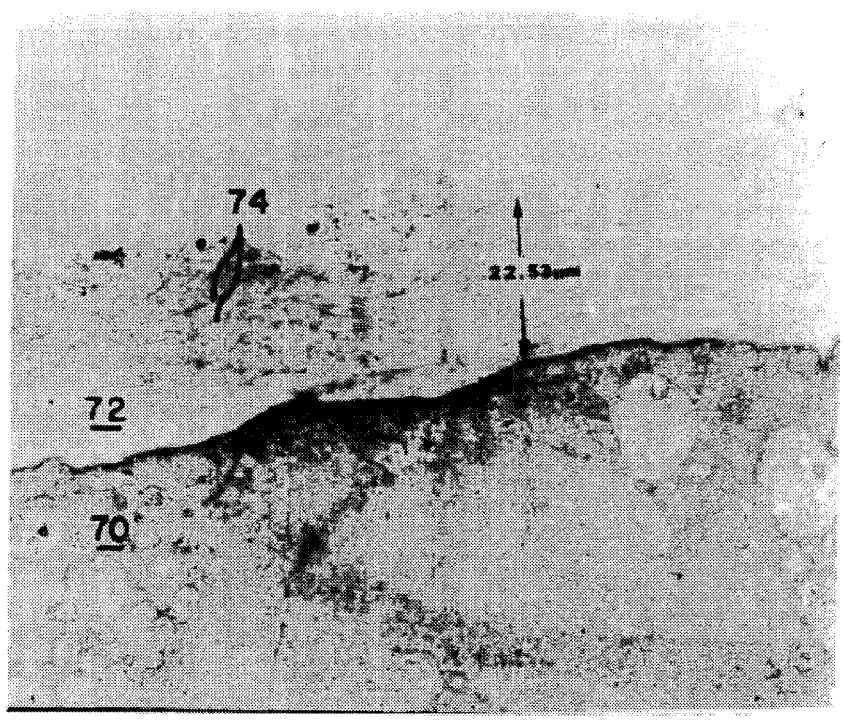
FIG. 4 is a transmission electron micrograph of a retina and vitreous prior to the operative method of the invention.
Figure 5:
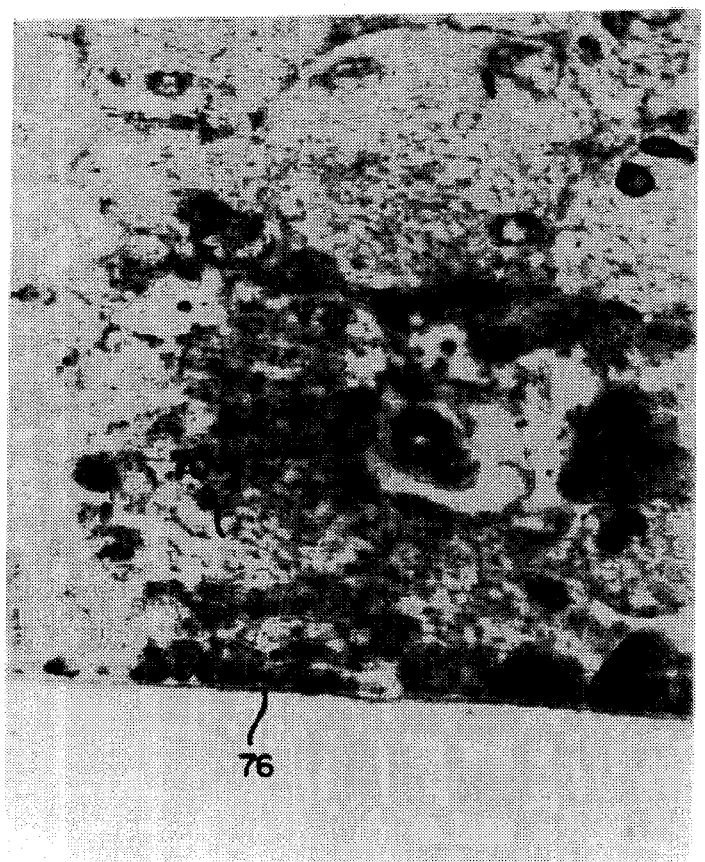
FIG. 5 is a transmission electron micrograph of a retina after the operative method of the invention.

FIGS. 4–5 are transmission electron micrographs of a cross-section of a retina 70. A standard vitrectomy was performed, the cortical vitreous was removed from only part of the retina using the methods described herein, and the retinal tissue was removed, fixed and prepped for standard transmission electron microscopy.

FIG. 4 shows the results following standard vitrectomy attempting to remove as much core vitreous as possible near the retina. Despite this effort, a residual amount of cortical vitreous can be seen as a layer 72 over the retina. The thin fibrils of collagen 74 are also visible.

FIG. 5 is a transmission electron micrograph of the same retina at the same magnification as in FIG. 4, but showing the section after removal of the cortical vitreous using the methods of the invention. The double-layer structure 76 of the retina 70 is free of any cortical vitreous. The structural integrity of the retina is intact despite having removed the tightly adherent cortical vitreous.

Figure 6:
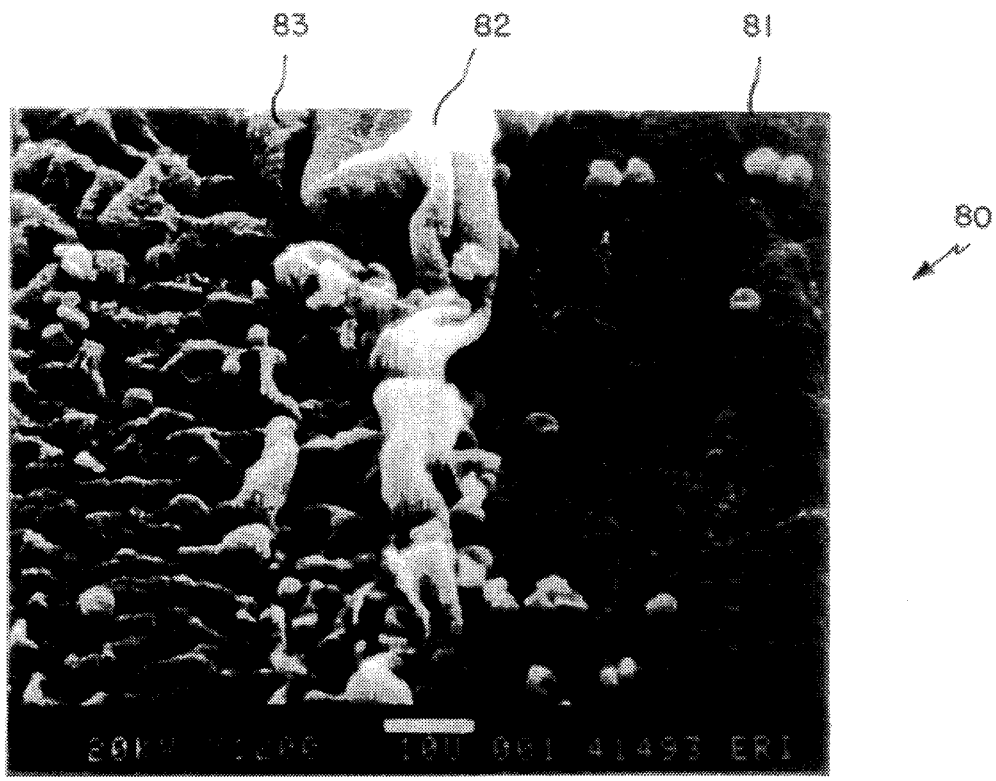
FIG. 6 is a scanning electron micrograph of a retina after the operative method of the invention.

Scanning electron microscopy was performed after cortical vitreous removal of part of a retina, as described above with reference to FIGS. 4–5. The tissue was fixed in standard fashion. FIG. 6 is a scanning electron micrograph at 1200 x taken of a retina 80 that had a partial stripping of the cortical vitreous. The line of demarcation 82 between denuded and non-denuded areas crosses the midline. The right half of the photograph, showing a smooth contour, is the denuded retina 81. The left side, which shows a convoluted surface, is covered with collagen fibrils 82 of the cortical vitreous 83.

Figure 7:
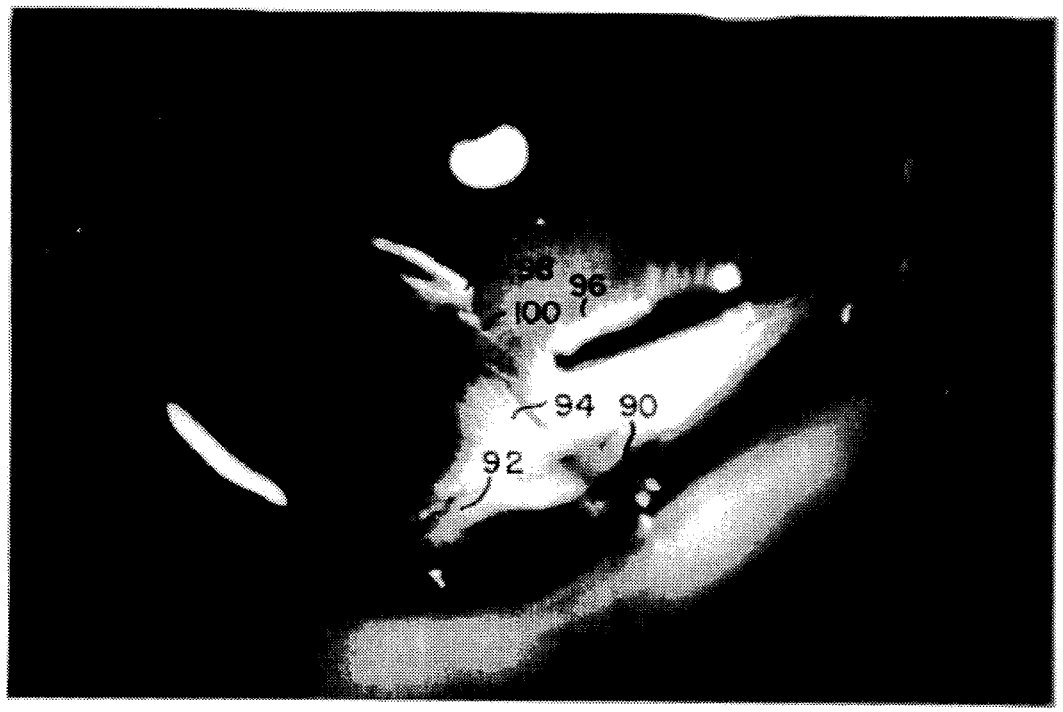
FIG. 7 is an intraocular photograph showing the optic nerve and cortical vitreous fibrils.

FIG. 7 is an intraocular photograph taken during surgery showing the optic nerve 90 from which blood vessels 92 emerge. Myelinated nerve fibers are visible as a layer 94 of thin strands. Just above the nerve fiber layer 94 is the inferior retina 96 covered by a thin layer of transparent cortical vitreous. After mechanical stimulation of the cortical vitreous by stroking with an intraocular forceps 98 for several minutes, thin collagen fibrils 100 within the cortical vitreous become visible. The forceps is then used to seize and elevate the cortical vitreous by the fibrils (supra.).

Utility

The methods of the invention are useful for epi-retinal implantation of any neural stimulation or sensing application in which retinal tissue surface contact is required. In particular, the methods, when used with the contact structure described herein, provides both the contacting surface and mechanical support of stimuli and sensory electronics and electrodes. Furthermore, the structure provides the ability for attachment to neural tissue in a location distant from an active stimulation location, thereby isolating any physiological degradation due to the attachment. And of equal importance, the contact structure inherently provides adequate surface pressure for contacting neural tissue, while at the same time minimizing that pressure due to its ability to easily conform to contours in neural tissue.

The methods of the invention are applicable to implantation of a wide range of stimulation prosthetics for visual systems. Furthermore, the methods of implantation will allow for engagement and adherence of implantable systems for use in physiological studies of the eye and retina. Thus, the methods may also be employed to implant systems to measure chemical and physical parameters like oxygen, carbon dioxide, pH, calcium, glucose, or temperature and pressure, and may provide an method for implanting a mechanism for use as a chemical dispersement system to disperse chemicals into the eye and retina.

Equivalents

It should be understood that various changes and modifications of the preferred embodiments may be made within the scope of the invention. Thus it is intended that all matter contained in the above description be interpreted in an illustrative and not limited sense.

I claim:

1. A method for removing a cortical vitreous of an eye, comprising:

transforming a cortical vitreous from a transparent to a visible condition by mechanically stimulating the transparent cortical vitreous to induce formation of collagen fibrils and contraction thereof; and separating at least a portion of the cortical vitreous from an adherent retinal surface to form an epi-retinal space.

2. The method of claim 1, further comprising introducing an object to be implanted into the epi-retinal space; and engaging said object with a surface of said retina that is free of said cortical vitreous.

3. The method of claim 2, further comprising adhering said object to said surface of said retina after engagement therewith.

4. The method of claim 2, which further comprises anchoring a first portion of said object to said retinal surface, and contacting said retinal tissue with a second portion of said object which is interconnected with said first portion via an interconnection, wherein said interconnection exhibits a weak restoring force which, in conjunction with the geometry of said second portion, provides a preselected desired pressure of contact against said retinal surface.

5. The method of claim 4, wherein said second portion comprises a mechanical support for a stimulating an electrode structure positioned on said second portion for stimulating neurons within said retina.

6. The method of claim 4, wherein said first portion and said second portion together comprise an integral structure.

7. The method of claim 6, wherein said integral structure comprises a cantilever.

8. A method for implanting an object on a retina of a subject, comprising:

inducing contraction of at least a portion of a transparent cortical vitreous of the subject so that at least a portion is rendered visible by mechanically stimulating the transparent cortical vitreous to induce formation of collagen fibrils and contraction thereof;

separating said visible cortical vitreous from an underlying retina;

forming an epi-retinal space defined between said retina and said separated cortical vitreous;

enlarging said epi-retinal space;

introducing an object into said epi-retinal space; and engaging said object within the retina that is free of said cortical vitreous.

9. The method of claim 8, further comprising adhering said object to said retinal tissue that is free of said cortical vitreous.

10. The method of claims 8 or 9, wherein the step of inducing contraction comprises introducing an inducing element onto said at least a portion of the cortical vitreous of the subject to render the cortical vitreous visible over an area of at least 10 millimeters.

11. The method of claim 8, wherein the step of enlarging the epi-retinal space comprises engaging and elevating said collagen fibrils of said cortical vitreous.

12. The method of claim 9, wherein the step of adhering comprises providing to said retinal tissue free of cortical vitreous a hydrophilic object that will adhere by virtue of its hydrophilic properties.

13. The method of claim 9, wherein the step of adhering comprises gluing said object to said retina free of said cortical vitreous.

14. The method of claims 9 or 12, wherein the step of adhering comprises providing a photocoagulating means to said object while engaged with said retina free of said cortical vitreous.

15. A method for removing a cortical vitreous from an inner surface of a retina of an eye, comprising:

removing vitreous material of the eye to expose the retina and associated cortical vitreous;

inducing contraction of at least a portion of the cortical vitreous of the eye so that said at least a portion of the cortical vitreous is rendered visible by mechanically stimulating the cortical vitreous to induce formation of collagen fibrils and contraction thereof;

separating said visible cortical vitreous from the retina; and removing said cortical vitreous.

16. The method of claim 15, further comprising forming an epi-retinal space defined between said retina and said separated cortical vitreous;

enlarging said epi-retinal space;

introducing a structure into said epi-retinal space; and engaging said retina that is free of said cortical vitreous with said structure.

17. The method of claim 16, wherein said structure that includes a first portion for attachment to a first location on a surface of the retina, and a second portion interconnected with said first portion via an interconnection and being held in contact with a second location on the retina adjacent to cells to be stimulated, said interconnection exhibiting a weak restoring force developed in response to curvature of said interconnection along an inner radius of the retina, whereby said weak restoring force in conjunction with a geometry of said second portion provides a preselected desired pressure of contact against said retina.

* * * * *